(12) United States Patent
Sarkela et al.

(10) Patent No.: US 11,980,461 B2
(45) Date of Patent: May 14, 2024

(54) METHOD AND SYSTEM FOR MONITORING DEPTH OF MUSCLE RELAXATION OF A PATIENT

(71) Applicant: GE Precision Healthcare LLC, Wauwatosa, WI (US)

(72) Inventors: Mika Olli Kristian Sarkela, Helsinki (FI); Mari Johanna Partio, Espoo (FI)

(73) Assignee: GE Precision Healthcare LLC, Wauwatosa, WI (US)

(*) Notice: Subject to any disclaimer, the term of this patent is extended or adjusted under 35 U.S.C. 154(b) by 1033 days.

(21) Appl. No.: 16/569,261

(22) Filed: Sep. 12, 2019

(65) Prior Publication Data

US 2021/0076982 A1 Mar. 18, 2021

(51) Int. Cl.
*A61B 5/11* (2006.01)
*A61B 5/00* (2006.01)

(52) U.S. Cl.
CPC .......... *A61B 5/1106* (2013.01); *A61B 5/0002* (2013.01); *A61B 5/746* (2013.01)

(58) Field of Classification Search
None
See application file for complete search history.

(56) References Cited

U.S. PATENT DOCUMENTS

| 4,387,723 A * | 6/1983 | Atlee, III | A61B 5/1106 600/595 |
| 2009/0018610 A1* | 1/2009 | Gharib | A61B 17/02 607/48 |
| 2013/0204156 A1* | 8/2013 | Hampton | A61B 5/4848 600/546 |

OTHER PUBLICATIONS

Neil R. Connelly et al., Subjective Responses to Train-of-Four and Double Burst Stimulation in Awake Patients, 1990, p. 650-653.
Hans Soren Helbo-Hansen et al., The Accuracy of Train-of-four Monitoring at Varying Stimulating Currents, 1992, 76, p. 199-203.
Sorin J. Brull et al., Stimulation with Submaximal Current for Train-of-four Monitoring.

* cited by examiner

*Primary Examiner* — Alex M Valvis
*Assistant Examiner* — Aurelie H Tu

(57) ABSTRACT

A method of monitoring depth of muscle relaxation of a patient includes applying a series of stimulations to a nerve of a patient and measuring muscle responses thereto. A maximal stimulus current, a supramaximal stimulus current, and/or a submaximal stimulus current are determined based on the muscle responses, wherein the maximal stimulus current is a current at which a maximal muscle response is produced from stimulating the nerve, the supramaximal stimulus current is greater than or equal to the maximal stimulus current, and the submaximal stimulus current is less than the maximal stimulus current. A first set of stimulations are applied to the nerve of the patient. Either the supramaximal stimulus current or the submaximal stimulus current are then selected for a subsequent series of stimulations based on the measured muscle responses to the first series of stimulations, and the subsequent series of stimulations are performed accordingly to monitor the patient's depth of muscle relation.

8 Claims, 8 Drawing Sheets

METHOD AND SYSTEM FOR MONITORING DEPTH OF MUSCLE RELAXATION OF A PATIENT

BACKGROUND

The present disclosure generally relates to medical patient monitoring, and more particularly to systems and methods for monitoring neuromuscular transmission to gauge depth of muscle relaxation of a patient to which a neuromuscular blocking agent has been administered.

Neuromuscular transmission (NMT) is the transfer of an impulse between a nerve and a muscle in the neuromuscular junction. NMT may be blocked in a patient undergoing a surgical procedure, for example, by neuromuscular blocking agents/drugs, which may cause transient muscle paralysis and prevent the patient from moving and breathing spontaneously.

Muscle relaxation is used during general anesthesia to enable endotracheal intubation and to provide the surgeon with optimal working conditions. At the end of a surgical procedure, the level of NMT is used to determine when the patient can be extubated. The level of neuromuscular block may be monitored to ensure appropriate block is provided for the given procedure and/or to determine when the patient can be safely extubated.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One embodiment of a method of monitoring depth of muscle relaxation of a patient includes applying a series of stimulations to a nerve of a patient and measuring muscle responses thereto. At least one of a maximal stimulus current, a supramaximal stimulus current, and a submaximal stimulus current for the patient are determined based on the muscle responses, wherein the maximal stimulus current is a current at which a maximal muscle response is produced from stimulating the nerve, the supramaximal stimulus current is greater than or equal to the maximal stimulus current, and the submaximal stimulus current is less than the maximal stimulus current. A first set of stimulations, such as a series of supramaximal stimulations, are applied to the nerve of the patient and muscle responses to the first set of stimulations are measured. Either the supramaximal stimulus current or the submaximal stimulus current are then selected for a subsequent series of stimulations based on the measured muscle responses to the first set of stimulations, and the subsequent series of stimulations are performed at the selected stimulus current and the muscle responses of the patient are measured to monitor the patient's depth of muscle relation.

One embodiment of a method of monitoring depth of muscle relaxation of a patient includes, prior to administration of a neuromuscular blocking agent to the patient, determining at least one of a maximal stimulus current, a supramaximal stimulus current, and a submaximal stimulus current for the patient. In one embodiment, the at least one of the current values is stored in a storage medium associated with a sensor device. The maximal stimulus current is a lowest current at which a maximal muscle response is produced from a stimulation to a nerve of the patient, the supramaximal stimulus current is greater than or equal to the maximal stimulus current, and the submaximal stimulus current is less than the maximal stimulus current. After administration of the neuromuscular blocking agent to the patient, periodically applying a train-of-four (TOF) stimulation to the nerve of the patient at the supramaximal stimulus current and measuring TOF response to the supramaximal stimulations. In one embodiment, a supramaximal stimulation mode indicator is stored in a storage medium associated with a sensor device indicating that the supramaximal stimulation is being used to monitor the patient. Upon identifying that the measured TOF response is at least equal a supramax response threshold, periodically applying a TOF stimulation to the nerve of the patient at the submaximal stimulus current and measuring a submax TOF response to monitor the patient's depth of muscle relaxation. A submaximal stimulation mode indicator is stored in a storage medium associated with a sensor device indicating that the submaximal stimulation is being used to monitor the patient.

One embodiment of a system for monitoring depth of muscle relation of a patient includes a stimulator configured to apply a series of stimulations to a nerve of the patient and a sensor device configured to measure muscle responses of the patient to the series of stimulations. A storage medium and controller are also included. The storage medium is configured to store a stimulation mode indicator that indicates a stimulation mode for the stimulator and/or a stimulus current indicator of at least one of a maximal stimulus current, a supramaximal stimulus current, and a submaximal stimulus current for the patient, wherein the maximal stimulus current is a current at which a maximal muscle response is produced from stimulating the nerve, the supramaximal stimulus current is greater than or equal to the maximal stimulus current, and the submaximal stimulus current is less than the maximal stimulus current. The controller is configured to control the stimulator to apply a set of stimulations to the nerve of the patient at varying stimulus currents and measure muscle responses to the set of stimulations to determine at least one of the maximal stimulus current, the supramaximal stimulus current, and a submaximal stimulus current for the patient, and then to control the stimulator to periodically apply a TOF stimulation to the nerve of the patient at the supramaximal stimulus current and measure a TOF response to the supramaximal stimulations. The measured TOF response is compared to a supramax response threshold. Upon identifying that the measured TOF response is at least the supramax response threshold, the controller periodically controls the stimulator to apply a TOF stimulation to the nerve of the patient at the submaximal stimulus current and measures a submax TOF responses to monitor the depth of muscle relaxation of the patient. A submaximal stimulation mode indicator is stored in the storage medium.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1A:
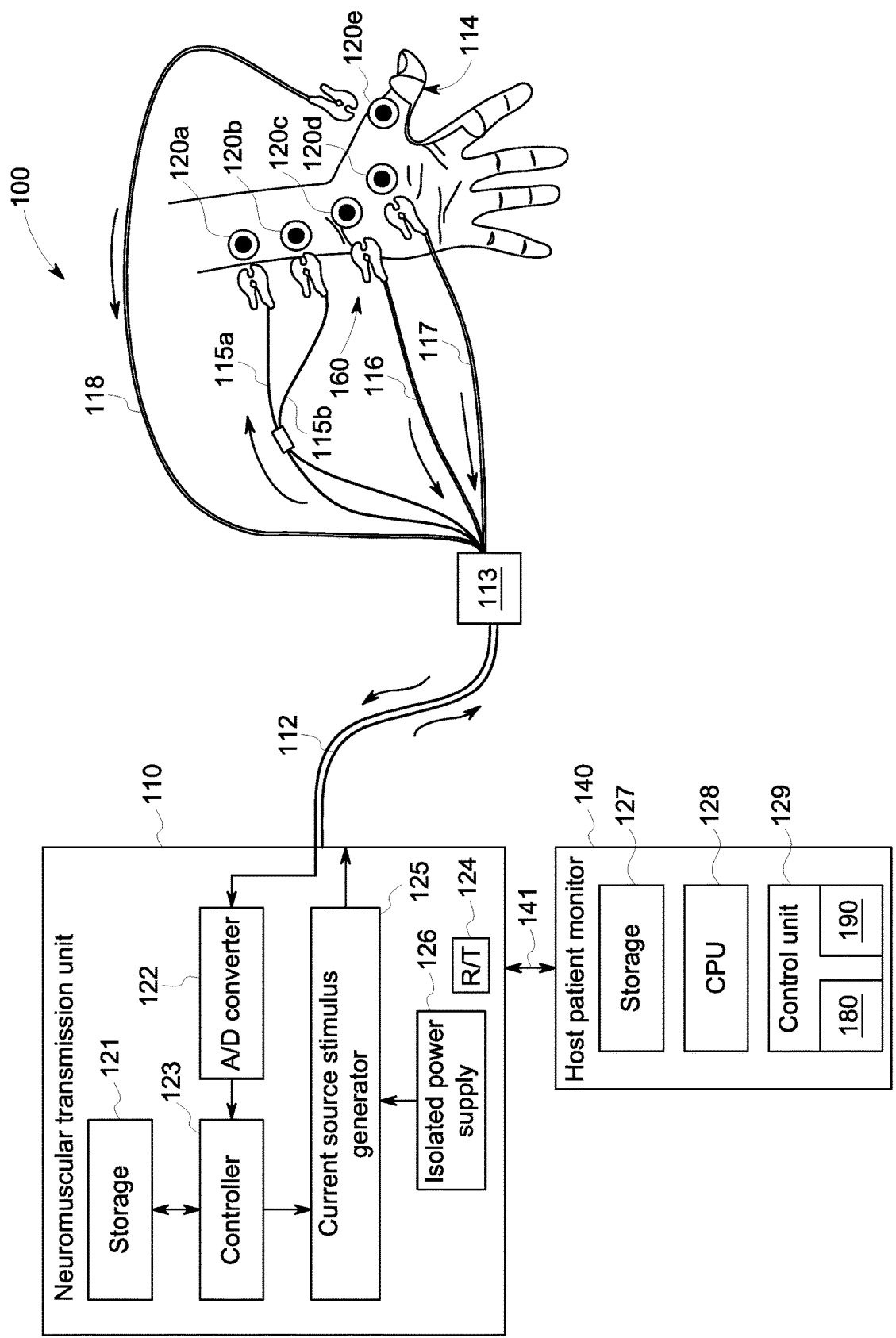
FIGS. 1A-1B depict exemplary neuromuscular transmission monitoring systems configured for monitoring depth of muscle relaxation of patient according to one embodiment of the present disclosure.

The following description relates to various embodiments of a neuromuscular transmission (NMT) monitoring system configured to monitor degree of neuromuscular blockage after the administration of muscle relaxants in patients (such as during surgery)—i.e., to measure a depth of muscle relaxation of a patient following administration of a neuromuscular blocking agent. Neuromuscular transmission (NMT) is the transfer of an impulse between a nerve and a muscle in the neuromuscular junction. NMT may be blocked by neuromuscular blocking agents/drugs, which may cause transient muscle paralysis and prevent the patient from moving and breathing spontaneously. Additionally, muscle relaxation may be used during general anesthesia to enable endotracheal intubation and to provide the surgeon with optimal working conditions. At the end of a surgical procedure, the neuromuscular block is reversed or allowed to wear off such that neuromuscular activity returns and the patient is able to breath unassisted before the removal of an endotracheal tube (i.e., extubation). Thus appropriate assessment of the degree of NMT block may be used for ensuring proper timing of extubation and of guiding intraoperative administration of neuromuscular blocking agents to maintain a desired degree of intraoperative neuromuscular block.

The inventors have recognized that continued NMT monitoring after extubation may be necessary in order to ensure patient safety and confirm the patient's ability to breathe unassisted. Residual neuromuscular blockade (RNMB) is postoperative condition where neuromuscular blocking agents exist in the neuromuscular junction. In order to reduce the likelihood of RNMB related complications, clinical guidelines instruct to ensure that TOF ratio of 90% is reached before patient is extubated. However, TOF 90% criterion does not provide full warranty for the avoidance of RNMB complications. RNMB complications are a health risk for patients following extubation, particularly where reversal agents are utilized and/or where the patient is extubated prior to reaching the recommended neuromuscular response level. Recurarization is defined as an increase in neuromuscular block after a period of recovery. Neuromuscular blockade reversals are often administered for accelerating recovery after paralysis; however, neuromuscular blockade reversals have limitations. If the dosage of the neuromuscular blockade is not correct, or if it is given too early, or if the reversal agent is metabolized faster than the neuromuscular blocking agent (particularly for long-acting NMBA's), then recurarization may occur. Additionally, other pharmacological interactions may occur to cause recurarization, which can be dangerous for the patient indicating a sudden drop of muscle function that could lead to ventilatory problems.

Accordingly, the inventors have developed the disclosed system and method that selectively utilizes lower stimulation levels that are sufficiently comfortable for the patient that NMT monitoring can be continued as a patient regains neuromuscular and respiratory capacity after surgical anesthesia, and even on awake patients. Typically, reliable and reproducible NMT monitoring involves nerve stimulation with supramaximal current, which is a current amount that is higher than the amount of current that produces a maximal stimulus response produced from stimulating a particular nerve. For example, supramaximal current is often 10% higher than the current producing a maximal stimulus response at the given nerve. When a patient/specific supramaximal current is used, all nerve endings of the stimulated nerve are activated. The strength of the maximal current for a particular patient typically depends, for example, on patient size. The maximal current depends also on the placement of stimulating electrodes in relation to the nerve to be stimulated. The supramaximal current is then defined based on the maximal current. Often, a supramaximal current may be, for example, in the range of 40 mA to 50 mA. One drawback of utilization of the supramaximal stimulation current is that it is painful for patients not under anesthesia and/or analgesics. Therefore, NMT monitoring using supramaximal current is typically not performed on awake patients.

The inventors have recognized that NMT monitoring may be continued for longer on a patient recovering from anesthesia, and may even be performed on awake patients if a submaximal stimulation current is used. Submaximal stimulation has not been incorporated in NMT monitoring algorithms for continued assessment of the depth of muscle relaxation for postoperative patient, particularly after extubation and during transfer to post anesthesia care unit (PACU). The inventors have recognized that submaximal current may be utilized to provide NMT monitoring that is sufficient to detect recurarization and to generate alarms accordingly so that appropriate patient care can be administered, such as reintubating or otherwise providing ventilation assistance to a patient. The inventors have recognized that as SpO2 monitoring may be insufficient for this purpose as it does not provide early detection of recurarization and may only identify the crisis after it has begun. Thus, the inventors endeavored to provide NMT monitoring that is sufficiently comfortable for a patient and is able to provide early detection of recurarization. While submaximal stimulation current may not necessarily activate all nerve endings, and therefore may be more subject to noise interference and signal variation, the inventors have recognized that NMT monitoring using submaximal current levels still provide sufficiently accurate and meaningful NMT results to facilitate early or advance detection of recurarization. As used herein, submaximal current refers to a current level that is less than the maximal current that produces the maximal stimulus response. Thus, the submaximal current is also less than the supramaximal current. To provide just one example, the submaximal current may be a preselected percentage of the maximal current, such as between 30% to 95% of the maximal current, or in another embodiment may be between 50% and 80% of the maximal current, or in another embodiment may be between 60% and 70% of the maximal current. Similarly, the submaximal current may be defined with respect to the supramaximal current instead of the maximal current.

The inventors have recognized that continued NMT monitoring using submaximal currents may be conducted by defining a threshold submaximal response threshold below which a recurarization alarm, or at least further testing for recurarization, is performed. The submax response threshold may be defined according to the desired level of sensitivity and specificity for detecting recurarization. In one embodiment, a recurarization alarm may be generated if the muscle responses to a submaximal train-of-four (TOF) stimulation is less than or equal to 70%. In another embodiment, the submax response threshold may be equal to the supramax response threshold. A person having ordinary skill in the art will recognize that other response thresholds may be utilized for detecting recurarization such as a different train-of-four ratio percentage or based on trend or other analysis for detecting a decrease in the muscle responses to the submaximal stimulus. In certain embodiments, initial detection of recurarization based on the submaximal muscle responses may be confirmed or rejected by conducting a supramaximal measurement utilizing the supramaximal stimulus current.

The inventors have also recognized that current NMT systems and methods need to be adapted in order to provide and/or enable continued NMT monitoring for a patient post operatively. For example, where multi-modality host patient monitors are utilized, current stimulation mode indicators and/or the patient-specific stimulation current values may be stored in storage device such that the information is available when the patient monitoring changes from the operating room monitor to a transport monitor and/or to a post anesthesia care unit (PACU). Thus, the inventors have developed a system and method where the patient-specific stimulus current values and/or the current stimulus mode (e.g. supramaximal or submaximal) are stored in storage device located in the NMT cable or in the NMT sensor. If a stand-alone NMT device is utilized which continues monitoring the patient throughout transport and PACU care, then those values may be stored in the device itself. Alternatively, the values can be stored to another accessible medium, such as data server accessible via hospital network or internet.

A NMT monitor may be used to monitor muscle responses to electrical stimulation of a motor nerve (e.g. ulnar nerve). For example, an electrical stimulus may be provided near the ulnar nerve at the wrist and the response of the muscle near the thumb, adductor pollicis, may be monitored. In clinical settings, a nerve stimulator is attached to on top of a motor nerve of the patient and an electrical stimulation current is applied to the patient before induction of anesthesia or at least prior to administration of a neuromuscular blocking agent. A reference value for the muscle responses is recorded by the NMT monitor and it may be used to normalize the muscle responses once the muscle relaxant is administered. In one embodiment, maximal stimulus current is defined with a sweep of increasing stimulation currents and measuring subsequent muscle responses. The point where strength of muscle response is not increased anymore by the increasing stimulus current is defined as the maximal stimulus current. For example, giving 20 mA stimulus and measuring response, 25 mA stimulus and measurement, 30 mA etc. When measured response reaches plateau, maximal stimulus current is obtained. Once stimulus current is defined, TOF monitoring modality can be started. In TOF, four successive supramaximal stimuli are provided. As described above, the supramaximal stimulus current is a stimulus current amount that is greater than or equal to the maximal stimulus current, such as a preselected percentage greater than the maximal current. In one non-limiting example, the supramaximal stimulus current is 10% greater than the maximal stimulus current. Setting supramaximal stimulus current higher than the maximal stimulus current may be a preferred option because the effect that the stimulus current causes to the nerve may drift during the monitoring period. The drift may be caused by the weakening in the electrode impedances of the stimulator, or by varying patient temperature, for example. The submaximal stimulus current is a current amount less than the maximal stimulus current, such as a preselected percentage of the maximal or supramaximal currents. To provide one non-limiting example, the submaximal current may be defined as 66% to 77% of the maximal stimulus current (or 60% to 70% of the supramaximal stimulus current). In various embodiments, one or all of these values may be stored in a storage device associated with the NMT cable or the NMT sensor. Where only one such value is stored, the system may be configured to calculate the other patient-specific values based on the stored values and in accordance with a pre-defined relationship or proportions of the supramaximal and submaximal currents with respect to the maximal stimulus current value.

The evoked muscle responses may then be monitored through the measurement of electrical response of the muscle (electromyography (EMG)). In EMG, multiple electrodes may be used to record the compound muscle potential evoked by the stimulus. According to embodiments disclosed herein, neuromuscular transmission monitoring may be performed by measuring the electrical potentials at the muscle via an electromyography (EMG) sensor receiving bioelectric potentials captured by EMG electrodes, in response to an electric stimulation of a motor nerve. Exemplary neuromuscular transmission monitoring systems configured to monitor depth of patient relaxation are provided in FIGS. 1A and 1B. The NMT monitoring system may include one or more electrodes which detect electrical activity of a muscle (referred to as EMG electrodes) in response to nerve stimulation, and a nerve stimulator. The NMT monitoring systems of FIGS. 1A and 1B also include a computing system, including controller 123 which may store instructions thereon, to carry out one or more control routines for determining a muscle response baseline, such as maximal muscle response, as well as monitoring neuromuscular block in patients during surgery and post-surgery during recovery.

In addition to EMG based NMT measurement modality, other modalities exist and may be employed in conjunction with the disclosed method and system for monitoring depth of muscle relaxation. Mechanomography (MMG) measures the force of thumb bending utilizing a force transducer and is typically assisted with a preload. Acceleromyography (AMG) may use piezo-electric ceramic wafer for estimating thumb acceleration as a response to stimulus. Still one modality is kineomyography (KMG) which utilizes piezo-electric sensor for measuring thumb bending as a response to stimulus (e.g., via mechano-sensing arrangement 114). Phonomyography (PMG) measures sounds generated by the muscle contraction. As will be evident to a person having ordinary skill in the art reviewing this disclosure, the inventive methods and systems described herein are applicable in all neuromuscular transmission (NMT) measurement modalities.

FIG. 1. illustrates one exemplary neuromuscular transmission (NMT) monitoring system 100 that is configured to monitor neuromuscular activity and depth of muscle relaxation via EMG/KMG techniques. NMT monitoring system 100 includes a neuromuscular transmission unit 110 which is communicatively coupled to a host patient monitor 140 via a communication link 141. The NMT unit 110 includes a plurality of neurostimulators, e.g., 115a and 115b, for providing stimulation output (e.g., electrical stimuli) of varying type and frequency to the patient and at least one input connected to one or more transducers for monitoring the evoked muscle responses in response to the electrical stimuli provided by the neurostimulators. The transductors include a sensor device, such as an EMG sensor 160 consisting of a plurality of electrodes for measuring the action potential of muscle contraction and/or KMG sensor 114 for measuring bending of the thumb in response to nerve stimulation. The signals detected by the sensor device may then be converted into digital signals by the A/D converter 122 of neuromuscular transmission unit 110.

In the depicted example, neurostimulators 115*a* and 115*b* are connected to stimulating electrodes 120*a* and 120*b*, respectively, which may apply an electrical stimulus to the patient's ulnar nerve at a pre-determined time interval. The amount of electrical stimulation provided to the neurostimulators is controlled by a current source stimulus generator 125 which receives commands signals from controller 123. In one embodiment, controller 123 is linked to the user interface of control unit 129, which comprises of a display unit 190 and buttons/knobs 180. The type and frequency of the stimulation output may be adjusted by the user via pressing buttons or knobs 180 on the patient host monitor 140. In one example, the type and frequency of the stimulation output may be adjusted by the user via pressing buttons or knobs 180 on the patient host monitor 140. In one example, neurostimulators 115*a* and 115*b* may be two wires of positive and negative charges, which may be attached by alligator clips or other attachment means to stimulating electrodes 120*a* and 120*b* on the skin of the patient's forearm.

A power supply (not shown) may supply electricity to an isolated power supply 126 which in turn provides power to current source stimulus generator 125. The controller 123 may be connected to the current source stimulus generator 125 to adjust the amount of electric current provided to the neurostimulators 115*a*-115*b*. The current stimulus generator 125 may generate different types of neurostimulation including train-of-four (TOF), single twitch (ST), double burst (DBS), post-tetanic count (PTC), current range (e.g., 1-70 mA with 1 mA steps), pulse width/frequency (e.g., 100, 200, 300 µs, or 1 Hz, 2 Hz, etc.). Further, the types of neurostimulation may be chosen via a manual or an automatic stimulating mode. If a manual stimulating mode is chosen, then the user may input the desired neuromuscular stimulating types, current range, and pulse width and/or frequency via pressing button 180 of the host patient monitor 140, for example. Alternatively, if a touch-screen is used as a display unit (e.g., display unit 190 of host patient monitor 140), then user input may be provided via touch input to the touch-screen on the display unit.

If an automatic neurostimulation mode is chosen, controller 123 of NMT unit 110 may select a first neurostimulation type as its default setting, such as TOF stimulation, and based on the muscle response signals received from the EMG/KMG sensor the controller reports the muscle response signals to the user by displaying graphs and numbers (e.g., via display unit 190 of host patient monitor 140). The display unit 190 may display the muscle response data/information to the user and may also include alarm signals/message for alerting the user of potential sensor error.

Additionally, NMT unit 110 may be connected to a host patient monitor 140 through a communication link 141. Host patient monitor 140 may include storage device 127, CPU 128, and control unit 129. Storage device 127 may have similar functions as storage device 121. Control unit 129 may include control buttons/knobs 180 and display unit 190. The control buttons and knobs of control unit 129 may be configured to allow for user input. The display unit 190 may be configured to receive touch input from a user.

One preferred neuromuscular stimulating output of the present disclosure is a train-of-four (TOF). In one example, TOF may typically use four brief (between 100 and 300 µs) stimulation current pulses (generally less than 70 mA) at 2 Hz, periodically conducted every 10 to 20 seconds as electrostimulation. The resulting twitches (i.e. muscle responses) may each be measured and quantified for electromyography response via EMG sensor—i.e., the TOF response. In one embodiment the TOF response is determined by comparing the first twitch (referred to as the T1 twitch) and the last twitch (referred to as the T4 twitch). The ratio of the last twitch to the first twitch (referred to as TOF ratio) may provide an estimate of the level of neuromuscular blockade (e.g., depth of relaxation) experienced by the patient. The TOF ratio may range from 0 to 100%, for example, in addition to the TOF ratio, another ratio that can be calculated during TOF stimulation is referred to as TO2. TO2 is the ratio of the second twitch (T2) to the first twitch (T1) in the train-of-four stimulation pulses. The electrical TOF stimuli series may be spaced by ten or more seconds (generally 20 seconds is used to provide a margin of safety) to give a rest period for full restoration of steady-state conditions, as faster stimulation results in smaller evoked responses. TOF stimulation is the most commonly used technique for monitoring the neuromuscular blockade in lightly-blocked patients as well in patients that are recovering from neuromuscular block; however other stimulation methods may be utilized and are within the scope of the present disclosure.

EMG sensor 160 may include a plurality of electrode connections 116, 117, and 118 connected to sensing electrodes 120*c*, 120*d*, and 120*e*, respectively. Most commonly, the three sensing electrodes are positioned to give the most consistent EMG signals. In the depicted example, sensing electrode 120*e* is placed over the muscle, tendon, or finger, sensing electrode 120*d* is placed over the mid-portion of the muscle close to the neuromuscular junction, while sensing electrode 120*c* may be variable. In one example, electrodes 120*d* and 120*e* may be recording electrodes, while electrode 120*c* may be a grounding electrode. The grounding electrode provides a common reference for the EMG recording electrodes. For example, the recording electrode 120*d* may be placed on top of m. adductor pollicis in the thenar eminence and recording electrode 120*e* may be placed on top of the distal interphalangeal joint of the thumb, while the grounding electrode 120*c* may be placed at centerline over the flexor retinaculum at the palmar side of the wrist. EMG sensor 160 measures the magnitude of electrical activity sensed by electrodes 120*c*-120*e* in response to nerve stimulation and when received at the neuromuscular transmission monitor, is recorded as the EMG muscle response signal.

Stimulating electrodes 120*a*-120*b* and sensing electrodes 120*c*-120*e* may have mechanisms for improving electrical contact to skin such as conductive gel and mechanisms for improving fixation to the skin such as biocompatible adhesives placed beneath the electrodes. Further, the electrodes may be suitable electrodes, such as silver/silver chloride electrodes. Further, the electrodes may be disposable which can be discarded after a single-use. In another example, the stimulators (e.g., stimulators 115*a* and 115*b*) and the sensing connections (e.g. electro-sensing connections 116-118) along with their respective electrodes may be incorporated into a disposable sensing unit. In one example, the disposable sensing unit may be included as part of a glove which may be discarded after a single-use.

Further, information regarding the EMG muscle response signals received from EMG sensor 160 may be sent to NMT unit 110 via main connector 113 and cable 112. In one example muscle response signals from EMG sensor 160 sensor are fed into a signal scaling and filtering circuit (not shown). After scaling the signal and filtering noise, the signal may be converted from an analog signal to a digital signal in analog-to-digital (A/D) converter 122 and sent to a controller 123 for processing. Further, the muscle signal response signals may also be amplified via an amplifier (not shown) before being transmitted into the A/D converter 122. The controller 123, or processing unit, is connected to a storage device 121 and once the signals are processed, the signal data may be displayed on the display unit 190 of the host patient monitor. In one example, the processed signals may be transmitted to the host patient monitor 140 and displayed on the display unit 190 in real-time. Further still, the processed signals may be updated and stored in storage device 121. In embodiments, where the storage medium is not integrated to the sensor device 114/160 or cable connector 113', the storage device 121 may be used for storing the patient-specific stimulation current values and the stimulation mode. Storage device 121 may include any type of storage medium, or memory, including read-only memory (ROM) and random access memory (RAM), and a conventional data bus.

Figure 1B:
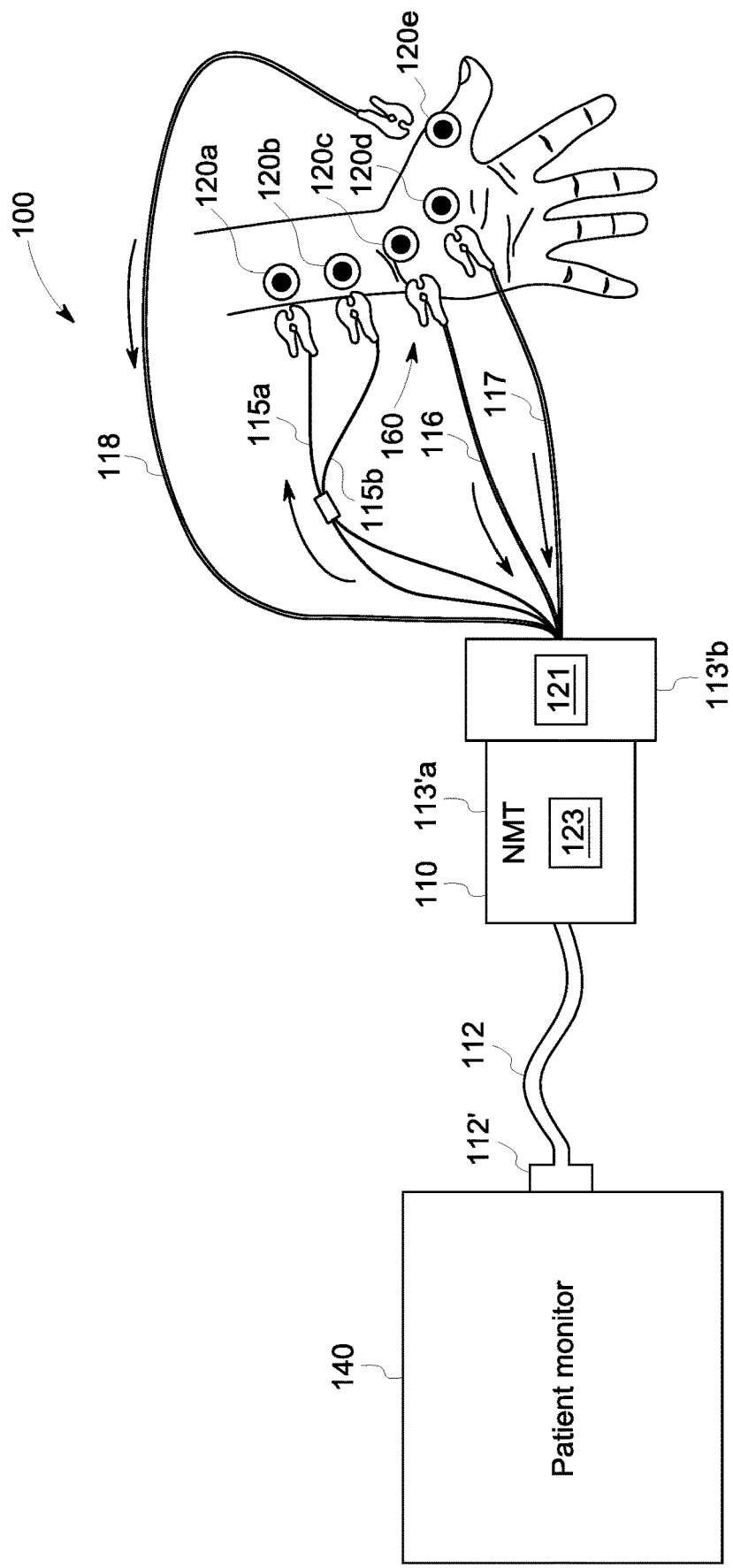

In certain embodiments, the NMT unit 110 may be incorporated into the transmission cable 112, and/or as part of a single device with the EMG sensor 160. FIG. 1B depicts one example of such an embodiment, where the NMT monitor 110 elements are incorporated and integrated with the cable connector 113', which is configured to connect with the host patient monitor or may otherwise be configured to connect with a host network of a healthcare facility, for example. The cable connector 113' may be integrated into and part of a physical cable 112 connecting the EMG sensor 160 and stimulator 115 to the patient monitor 140. In such an embodiment, the cable 112 may include a connector 112' configured to connect and disconnect from a patient monitor 140. Thus, for example, when a patient is moved and switched to a new monitor (such as to move from the operating room to post-op), the cable 112 will be disconnected from one patient monitor 140 and reconnected to another. Alternatively, part of the connection between the EMG sensor 160 and the patient monitor 140 may be wireless. For example, the cable 112 shown in FIG. 1B may instead be a wireless connection and the cable connector 113' may include a wireless transceiver 124 (see FIG. 1A) that provides a communicative link via a wireless protocol with the patient monitor 140. In such an embodiment, a wireless connection transition can be made when the patient is moved from one patient monitor 140 to another.

In the embodiment at FIG. 1B, the cable connector 113' includes two portions, including a reusable portion 113'a containing the elements of the NMT 110 (including the controller 123 as shown) and a disposable portion 113'b connected to the EMG electrodes 116-118 of the EMG sensor 160. In the depicted example, the EMG sensor 160 is connected to and integrated with the disposable portion of the cable connector 113'b, which is a disposable unit that includes the storage device 121 for storing the patient-specific stimulus current values and the stimulation mode. In other embodiments, the storage device may be incorporated with the EMG sensor 160 by other means, such as incorporated in a module connected to one of the electrodes. In all such embodiments, data of the storage device 121, such as stimulation currents and stimulation mode, can be accessed by the NMT unit 110.

The connector 113' comprising the NMT unit 110 and integrated EMG sensor 160, and/or the stimulator 115, stays with the patient during transition from the operating room to the PACU, and thus is configured to connect with different host patient monitors 140. For example, the disposable sensing unit contains stimulating electrodes 120a-b, EMG sensor 160 and the storage device 121. In a wireless embodiment, the NMT unit may have a wireless receiver/transmitter 124 (see FIG. 1A) configured to wirelessly communicate with the host patient monitor 140. In such an embodiment, the communication link 141 being a wireless communication link, may be via any of various wireless protocols, such as Bluetooth, Bluetooth low energy (DLE), ZigBee, or may be via the wireless medical telemetry service (WMTS) to provide a few examples.

An automatic calibration module may be stored in the storage 121 and executed by the controller to determine the optimum maximal stimulation current, submaximal stimulation current, and/or supramaximal stimulation current to provide to the patient based on the muscle response values received by the EMG electrodes, and based on the raw signals received from sensors, the module may determine a value, which may be used as a reference value for the neuromuscular blockade monitoring of the patient. At least one of the supramaximal, maximal, or submaximal current may then be stored in the storage device 121. The automatic calibration module may be performed when patient is not in paralyzed state. In other words, the automatic calibration module may utilize a reference value based on the signals received from the sensors when patient is in non-relaxed state (e.g., before the administration of the muscle relaxant).

The patient-specific value(s), such as the maximal, supramaximal, and/or submaximal current values are stored, such as in storage device 121 contained within the NMT unit 110 (which, as described above may be incorporated in the cable 112 or the sensor device 114/160). In other embodiments, the stimulation current value(s) may be stored in the cloud and may be accessible by one or more host patient monitors configured for monitoring the patient. Thus, such stimulation current value(s) may be accessible when NMT monitoring for the patient is switched between host monitors, such as in the transition from the operating room monitor to a transport monitor and/or a PACU monitor. For example, upon connection of the NMT unit 110 to a new host patient monitor 140, the NMT unit 110 may be configured to transmit the stimulation current value(s) and/or an indicator of the current stimulation mode (e.g. supramaximal or submaximal) to the new host patient monitor 140 so that stimulation and/or display of monitoring configuration and patient physiological data can be displayed accordingly.

Control unit 129 may also include a user interface (not shown) which can be used to control operation of the NMT monitoring system 100, including controlling the input of patient data, changing the monitoring parameters (e.g. stimulus type, current range, frequency/pulse width, etc.), and the like. The user interface may also include a graphical user interface configured for display on a display device, such as display unit 190. The graphical user interface may include information to be output to a user (such as muscle response signals, patient data, etc.) and may also include menus or other elements through which a user may enter input the control unit 129.

As discussed above, during neuromuscular stimulating of a patient to determine the depth of relaxation, train-of-four (TOF) stimulation is applied to the patient and the muscle response signals are received from EMG sensors for each of the four pulses of the stimulation. The TOF stimulation is applied to the patient at regular intervals, such as every 10-20 seconds and the resulting twitches (i.e. muscle responses) are measured and quantified for electromyography response by the EMG sensor 160.

Figure 2:
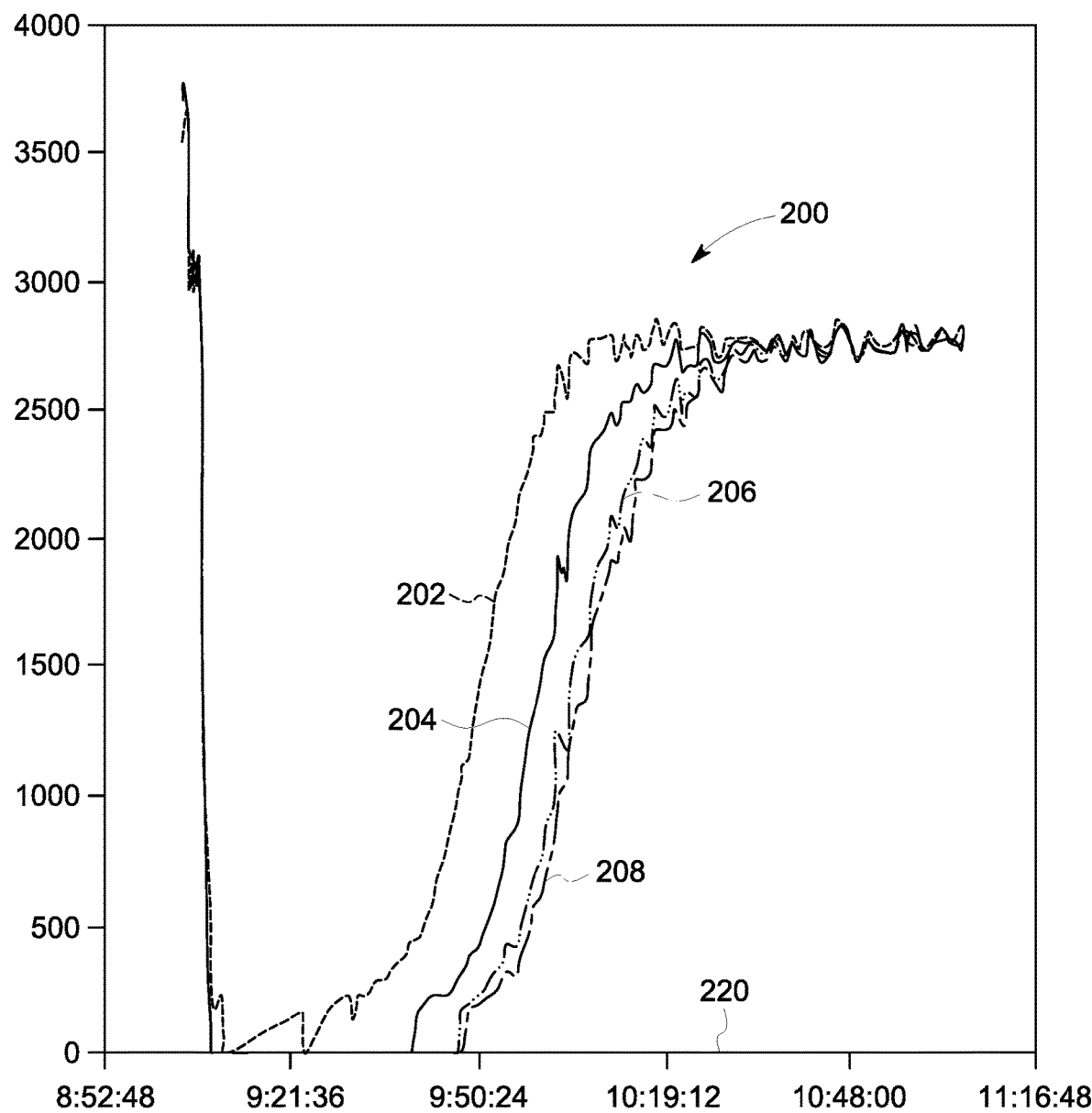
FIG. 2 is a graph showing muscle responses to a series of simulations, and particularly a train-of-four (TOF) stimulation.

FIG. 2 illustrates the EMG responses to each of the four pulses of a TOF stimulation over a measurement period set forth on this horizontal axis of the graph. The first twitch, referred to as the T1 twitch, is graphically illustrated by trace 202 in the graph 200. The second twitch, referred to as the T2 twitch, is shown by trace 204 while the third twitch, T3, is illustrated by trace 206. The last and final twitch, referred to as the T4 twitch, is shown by trace 208. As can be seen by the combined graph 200 of FIG. 2, the T1 trace 202 begins to be detected at the earliest point in time since the T1 twitch is in response to the first stimulation of the TOF simulation sequence. The T2, T3, and T4 twitches begin to be detected at a time slightly delayed from the detection of the T1 twitch, as is well known for a patient recovering from the neuromuscular blocking agent.

In well-known recovery monitoring methods, extubation of the patient may occur when the recovery of the patient reaches a recovery threshold at which the neuromuscular blocking has been diminished enough to support proper spontaneous breathing by the patient. In the present disclosure and many monitoring systems, the recovery threshold is based upon the TOF response, such as the ratio of the T4 twitch to the T1 switch (T4/T1), which is commonly referred to the TOF ratio or TOF %. As described previously, the TOF ratio may range between 0 and 100%. Typically, when the TOF ratio reaches 90%, extubation of the patient is considered to be safe. Thus, the relationship between the T1 twitch and the T4 twitch can be utilized to indicate depth of relaxation of the patient and to determining when the patient can be safely extubated. As can be understood with respect to FIG. 2, the TOF ratio of 90% occurs when the T4 trace 208 begins to closely correspond to the T1 trace 202.

Current relaxation depth monitoring methods and systems, such as using TOF stimulation, involve patient NMT monitoring until extubation. After extubation, NMT monitoring ceases and the patient's depth of muscle relaxation is no longer tested or tracked, which assumes that motor function is adequately and permanently recovered to support respiration. However, as described above, recurarization occurs in some patients and sometimes patients are extubated too early to guarantee autonomous respiration function, and thus the inventors developed the disclosed system that performs continued NMT monitoring of the patient's depth of muscle relaxation for a period of time until the risk of recurarization is negligible. Extubation is typically recommended when the muscle responses, such as the TOF response or TOF ratio, reaches 90% or higher. However, in practice extubation often occurs earlier and at lower muscle response levels. The disclosed system automatically determines when to switch to submaximal stimulation, which may be at the same threshold where extubation occurs, or at a different threshold. NMT monitoring then continues using the submaximal stimulation until either recurarization is detected, or the risk of recurarization becomes negligible. For example, NMT monitoring may continue in the submaximal mode for a period of time, or until a submax response threshold is reached, or may continue for the duration of PACU care.

Intensive care unit (ICU) patients may receive neuromuscular blocking agents for facilitating their intubation and ventilation. Some ICU patients may be still in their bed for weeks and are therefore in a risk for developing muscle weakness, even if they do not receive NMBA at all. NMT monitoring may be suitable tool for monitoring developing muscle weakness of ICU patients and submaximal stimulation current makes the long-term monitoring convenient for the patient. In ICU, practical NMT measurement interval can be 1-2 hours, for example. When developing muscle weakness is of interest, suitable neurostimulation type is, for example, ST, where single muscle response is compared to reference muscle response measured during NMBA clear period preferably in the early stages of hospital stay. For example, surgical patient can be first monitored with supramaximal stimulation mode in 20 seconds intervals during surgery. If the patient is transferred to ICU, monitoring may continue by switching supramaximal and submaximal stimulation mode in 10 minutes intervals for the first two days for detecting possible recurarization. If the patient stays in the ICU for extended period of time, monitoring may continue in submaximal stimulation mode in 1 hour intervals. During surgery and first two days of intensive care, neurostimulation type can be TOF. Afterwards neurostimulation type can be ST and the measured muscle response can be compared to the reference measurement T1, for example.

Figure 3:
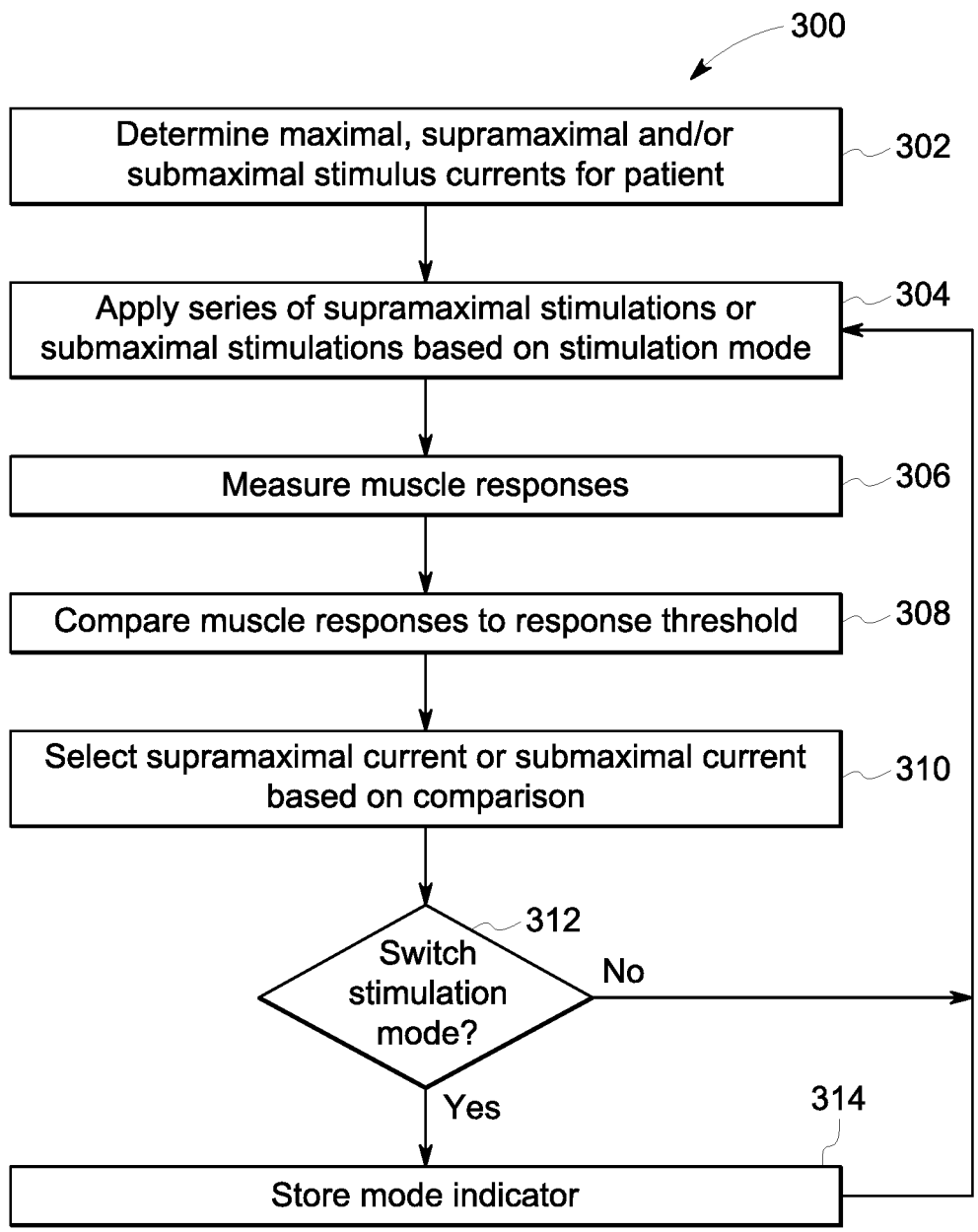
FIG. 3 is a flow chart demonstrating an exemplary embodiment of a method of monitoring depth of muscle relaxation according to the present disclosure.
Figure 4A:
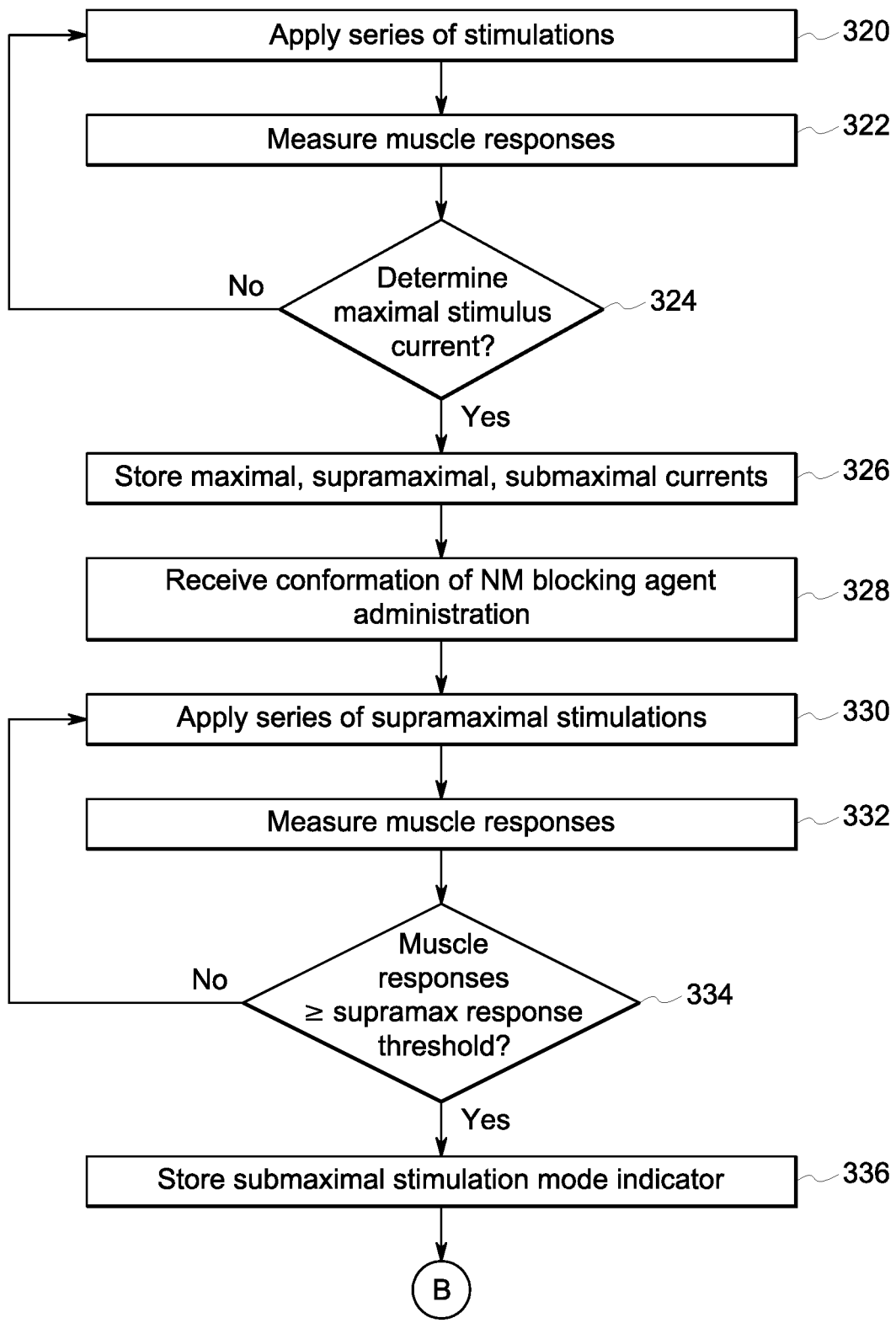
FIGS. 4A-4C depict embodiments, or portions thereof, of methods of monitoring depth of muscle relaxation of a patient in accordance with the present disclosure.
Figure 4B:
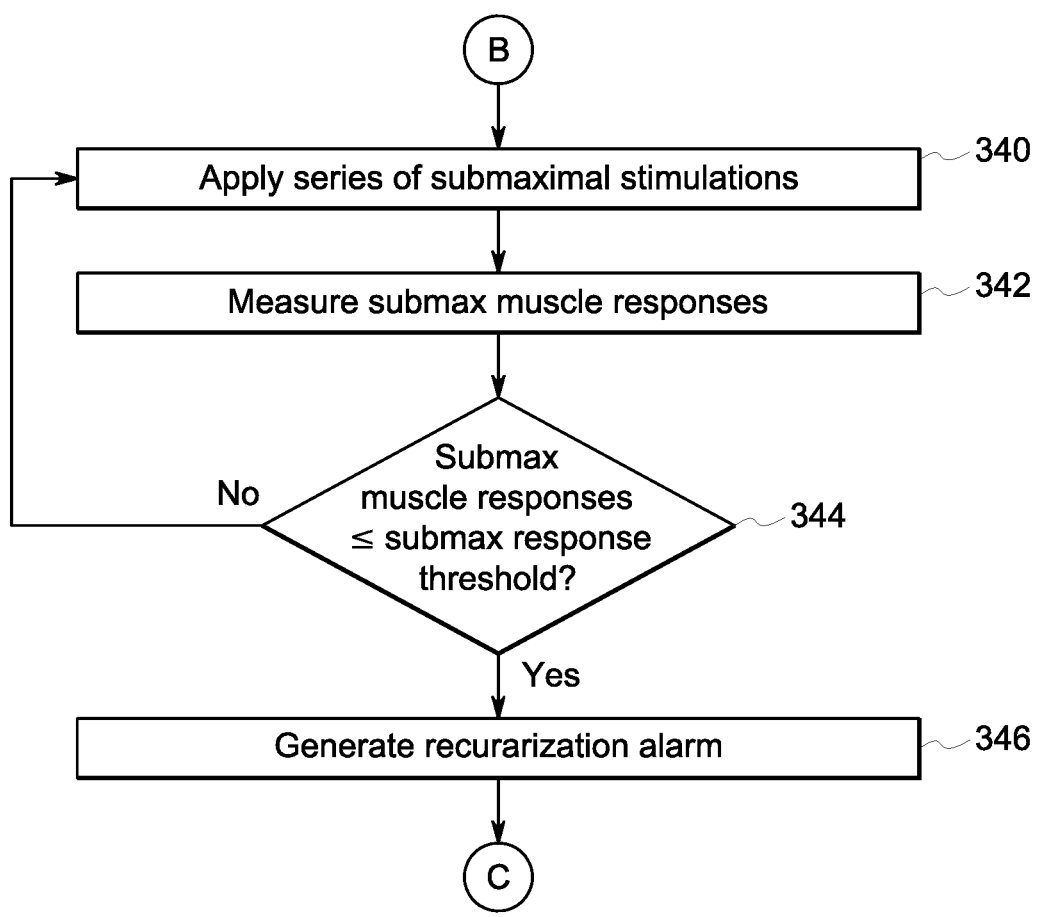
Figure 4C:
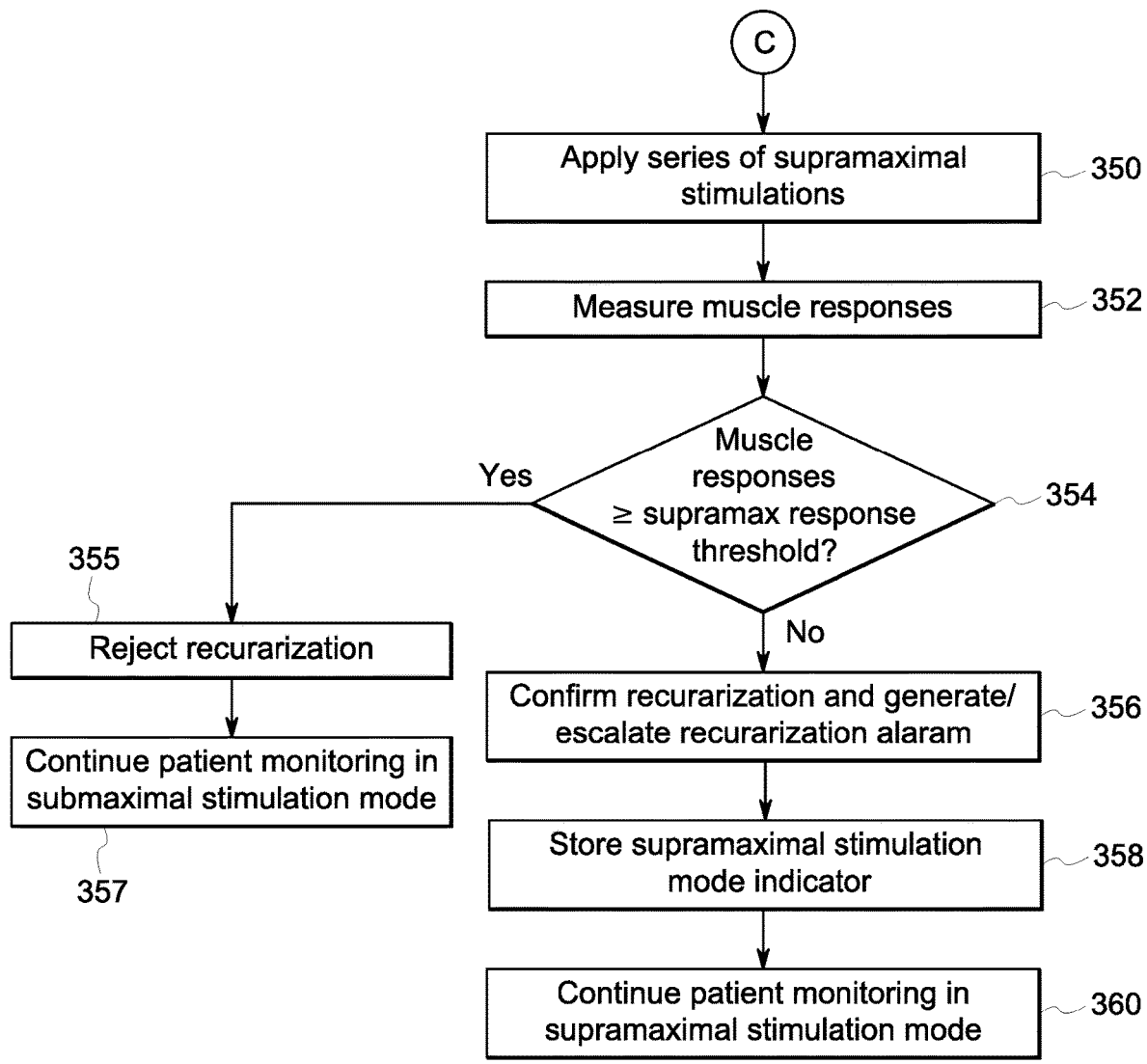
Figure 5:
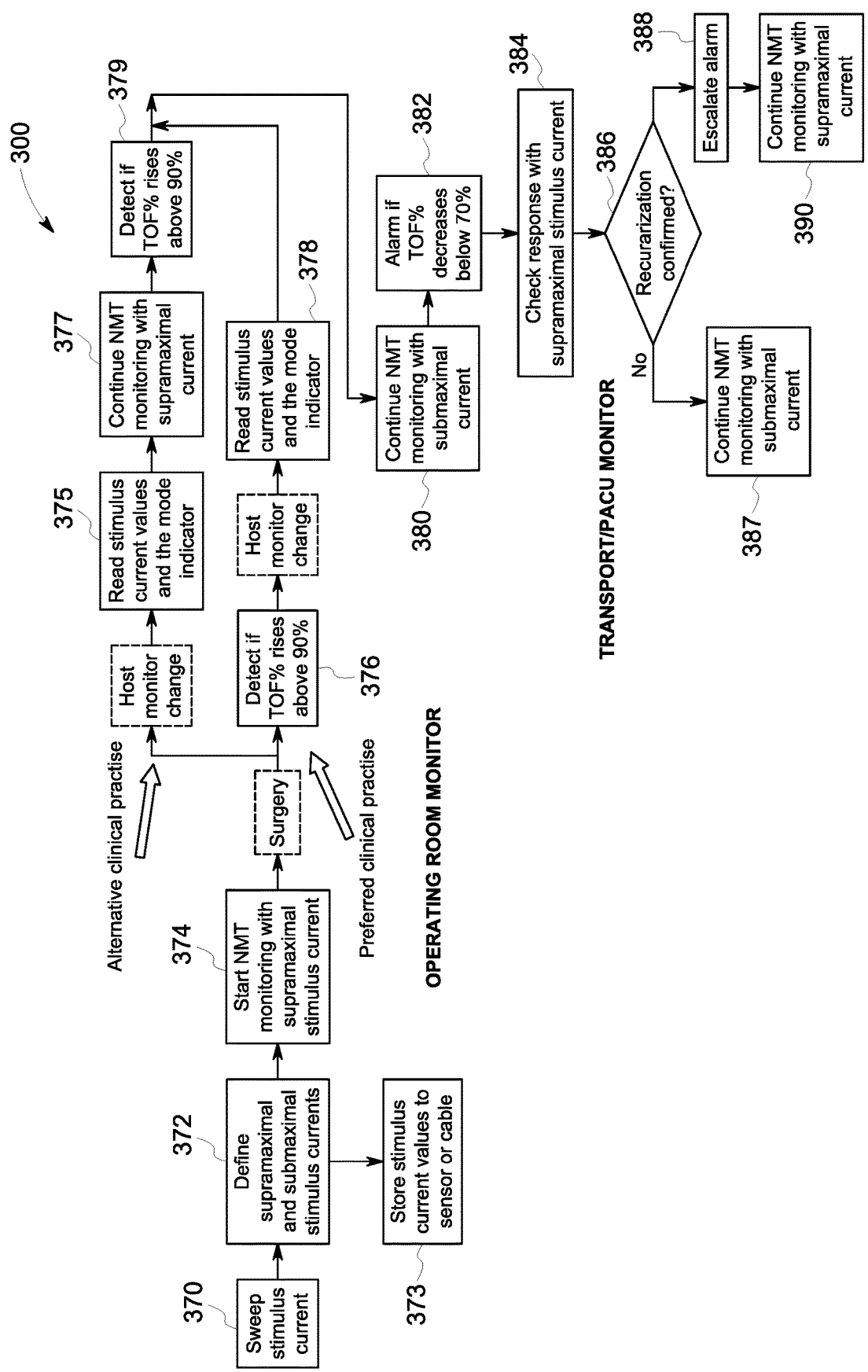
FIG. 5 depicts another embodiment of a method of monitoring depth of muscle relaxation of a patient in accordance with the present disclosure.

FIGS. 3 through 5 depict various embodiments, or portions thereof, of methods 300 of monitoring depth of muscle relaxation according to the present disclosure. In FIG. 3, one or more of the maximal stimulus current, supramaximal stimulus current, and the submaximal stimulus current are determined for the patient at step 302. A series of stimulations are then provided to the patient based on the stimulation mode at step 304. As is standard, the initial NMT monitoring may be conducted utilizing the supramaximal stimulation current. Muscle responses are measured at step 306 and the muscle responses are compared to an appropriate response threshold at step 308. For example, where supramaximal stimulus current is applied, the resulting muscle responses to the supramaximal stimulus may be compared to the supramax response threshold. For example, the supramax response threshold may be the threshold at which extubation is suggested or warranted, such as the 90% threshold discussed above. In other embodiments, the supramaximal current may be different than the 90% threshold, such as a lower threshold where extubation may be permissible with continued NMT monitoring at the submax stimulus level.

Accordingly, one of the supramaximal stimulus current or submaximal stimulus current is selected based on the comparison to the response threshold. For example, where the supramaximal stimulation current is used, and the muscle responses exceed the supramax response threshold, then the system may determine that switching to the submaximal stimulation mode is appropriate, and the submaximal stimulation current will be selected accordingly. As another example discussed in more detail below, if the submaximal stimulus is applied and the measured muscle responses are less than the submax response threshold, the supramaximal current may be selected and the system may determine that switching from the submaximal stimulation mode to the supramaximal stimulation mode is appropriate. If switching modes is selected at step 312, then a new mode indicator will be stored at step 314 indicating the stimulation mode is being applied. If a mode switch is not determined at step 312, then the system continues the next series of stimulations in the current mode and thus continues to periodically execute steps 304 through 310 applying the same stimulus level.

FIGS. 4A-4C each depict portions of the method 300, exemplifying embodiments thereof. A series of stimulations are applied at step 320, which may be a sweep stimulus current, and also responses are measured at step 322. The stimulation and response measurement is continued until the maximal stimulus current is identified at step 324. In certain embodiments the supramaximal and/or submaximal currents may also be identified based on the maximal stimulus current. The maximal, supramaximal, and/or submaximal currents are stored at step 326, such as in the storage device 121 of the NMT unit 110. In certain embodiments, these baseline determination steps may preferably be conducted prior to administration of the neuromuscular blocking agent. Once the neuromuscular blocking agent has been administered, confirmation thereof may be received at step 328. For example, a clinician may provide input, such as via a user interface on host patient monitor 140 or on the NMT unit 110 to commence measurement. Alternatively, the measurement may start with submaximal stimulation and the administration of neuromuscular blocking agent is detected based on the muscle responses. A series of supramaximal stimulations are then applied at step 330 and the muscle responses thereto are measured at step 332. For example, the series of supramaximal stimulations may be a TOF stimulation at the supramaximal current, and the measured muscle responses may be the TOF response consisting of up to four responses twitches. The measured muscle responses are then compared to the supramax response threshold. If the supramax response threshold is exceeded at step 334, then the system determines that submaximal stimulation mode should be applied for the next series of stimulations, and the submaximal stimulation mode indicator would be stored at step 336 indicating the mode switch. Otherwise, NMT monitoring continues the next series of stimulations in the supramaximal stimulation mode, each time measuring a new muscle response for assessment of the patient's depth of muscle relaxation, until such time as the muscle responses reach the supramax response threshold.

FIG. 4B depicts exemplary steps that may be executed in the submaximal stimulation mode. A series of submaximal stimulations are applied at step 340. Again, the series of submaximal stimulations may be, for example, TOF stimulations at the submaximal stimulation current. Submax muscle responses are recorded at step 342 in response to the series of submaximal stimulations. The submax muscle responses are then compared to a submax response threshold at step 344. NMT monitoring continues in the submaximal stimulation mode utilizing the submaximal stimulation current unless the submax muscle responses decrease and become less than the submax response threshold at step 344. In the depicted example, a recurarization alarm is generated at step 346 once the submax response threshold is exceeded. The next stimulation is then conducted at the supramaximal stimulation current in order to confirm or reject the detected recurarization.

FIG. 4C depicts exemplary steps for providing recurarization confirmation. A series of supramaximal stimulations are applied at step 350, and the muscle responses are measured at step 352. The muscle responses are compared to the supramax response threshold as described above. If, at step 354, the muscle responses exceed the supramax response threshold, then recurarization is rejected at step 355. In other words, if the measured muscle responses are sufficient to indicate nearly complete muscle response recovery, then it is determined that recurarization is not occurring. Given that the NMT monitoring in the submaximal stimulation mode may be subject to interference and/or mismeasurement due to the smaller stimulus, this confirmation process may be performed at least once in order to verify determinations made in the submaximal stimulation mode. In certain embodiments, the confirmation process may be performed prior to generating the recurarization alarm (i.e. prior to step 346 described above). If the recurarization is rejected at step 355, the NMT monitor may revert back to the submaximal stimulation mode and continue NMT monitoring in that submaximal mode at step 357. If, on the other hand, recurarization is confirmed, such as by the muscle responses being less than the supramax response threshold, then the recurarization alarm may be generated or escalated at step 356. The supramaximal stimulation mode indicator is then stored at step 358 and patient monitoring is continued in the supramaximal stimulation mode at step 360.

As described above, in certain embodiments, the system may be configured such that the NMT unit 110 moves with the patient and connects with various host patient monitors 140. FIG. 5 depicts one embodiment of a method 300 of monitoring depth of muscle relaxation where a host monitor change appears. A sweep stimulus current is applied at step 370, and the supramaximal and submaximal stimulus currents are defined at step 372, as is described above. The stimulus current value(s) are stored at step 373, such as in the storage device 121 that may be on the cable 112, such as in the connector 113 or some other element incorporated along the length of the cable 112, or incorporated in the sensor device 114/160. NMT monitoring then commences at step 374 utilizing the supramaximal stimulus current. The NMT monitoring continues throughout the surgical procedure where a neuromuscular blocking agent is utilized. Post-surgery, the patient is monitored to determine when extubation may occur and to detect recurarization. In one example, the rise of the train-of-four response, such as the TOF ratio, rises above 90% (step 376) prior to extubation, and the patient is then moved to PACU where a host monitor change occurs. Upon detection of the supramax response threshold of 90%, the system determines that switching to the submaximal stimulation mode is appropriate and stores the submaximal stimulation mode indicator, such as in storage 121 of the NMT unit 110. Upon connection to the new host monitor, the new host monitor reads the current stimulus value and/or the mode indicator from the storage device of the NMT unit 110.

In the alternative clinical practice, the patient may be extubated before detection of the 90% supramax response threshold, and thus while the system is still operating in the supramax stimulation mode. In such an embodiment the mode indicator read by the new host monitor will indicate the supramaximal stimulation mode at step 375, and thus NMT monitoring will continue in the supramaximal mode at step 377. Once the supramax response threshold is detected at step 379, then the system automatically switches to the submaximal stimulation mode and stores the mode indicator accordingly. NMT monitoring is then continued in the submaximal stimulation mode at step 380. If the measured muscle responses, such as indicated by the TOF ratio, decreases below 70% (as represented at step 382), then the recurarization verification is performed using the supramaximal stimulation current at step 384. If recurarization is confirmed at step 386, then the alarm is escalated at step 388, such as to generate an alarm at a nurse's station, automatically page a clinician, etc. NMT monitoring is then continued in the supramaximal stimulation mode at step 390. If, on the other hand, the supramaximal response does not confirm recurarization, and is instead greater than or equal to the submax response threshold, then the NMT monitoring is continued in the submaximal stimulation mode at step 387.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. A method of monitoring depth of muscle relaxation of a patient, the method comprising:

applying, by an electrode, a series of stimulations to a nerve of a patient and measuring muscle responses thereto;

based on the muscle responses, determining, by a processor, at least one of a maximal stimulus current, a supramaximal stimulus current, and a submaximal stimulus current for the patient, wherein the maximal stimulus current is a current at which a maximal muscle response is produced from stimulating the nerve, the supramaximal stimulus current is greater than or equal to the maximal stimulus current, and the submaximal stimulus current is less than the maximal stimulus current;

applying, by the electrode, a first set of stimulations to the nerve of the patient and measuring first muscle responses to the first set of stimulations; and selecting, by the processor, one of the supramaximal stimulus current and the submaximal stimulus current for a subsequent series of stimulations based on the first muscle responses to the first set of stimulations, the selecting comprising:

determining whether the first muscle responses to the first set of stimulations are at least equal to a supramax response threshold indicating muscle relaxation has succeeded to a level in which the patient can be safely extubated;

based on the first muscle responses being at least equal to the supramax response threshold, selecting the submaximal stimulus current for the subsequent series of stimulations; and based on the first muscle responses being less than the supramax response threshold, selecting the supramaximal stimulus current for the subsequent series of stimulations;

applying, by the electrode, the subsequent series of stimulations at the selected one of the supramaximal stimulus current and the submaximal stimulus current to the nerve of the patient and measuring muscle responses thereto;

comparing the muscle responses to the subsequent series of stimulations to a first threshold; and based on the muscle responses to the subsequent series of stimulations being below the first threshold, generating an alarm.

2. The method of claim 1, based on the submaximal stimulus current for the subsequent series of stimulations being selected, further comprising periodically applying a series of submaximal stimulations to the nerve of the patient at the submaximal stimulus current and measuring submax muscle responses to monitor the patient's depth of muscle relaxation.

3. The method of claim 2, further comprising identifying that the measured submax muscle responses are less than the first threshold, and then selecting the supramaximal stimulus current for a next series of stimulations.

4. The method of claim 3, wherein the alarm is generated based on the measured submax muscle responses being less than the first threshold.

5. The method of claim 3, further comprising:

applying the next series of stimulations at the supramaximal stimulus current and measuring muscle responses thereto;

comparing the first muscle responses to the supramax response threshold to confirm or reject recurarization;

if recurarization is confirmed, generating the alarm; and if recurarization is rejected, then selecting the submaximal stimulus current for the next series of stimulations.

6. The method of claim 1, where the series of stimulations are train-of-four (TOF) stimulations, and wherein the first muscle responses are four responsive muscle twitches.

7. The method of claim 6, further comprising:

determining a TOF response based on the first muscle responses;

wherein determining whether the first muscle responses are at least equal to the supramax response threshold includes comparing the TOF response to the supramax response threshold, and then selecting one of the supramaximal stimulus current and the submaximal stimulus current for the subsequent series of stimulations based on a result of the comparison.

8. The method of claim 1, wherein the supramaximal stimulus current is a preselected percentage greater than the maximal stimulus current determined for the patient, and wherein the submaximal stimulus current is a preselected percentage less than the maximal stimulus current or the supramaximal stimulus current.

* * * * *